United States Patent [19]
Thompson et al.

[11] Patent Number: 5,436,566
[45] Date of Patent: * Jul. 25, 1995

[54] LEAKAGE CAPACITANCE COMPENSATING CURRENT SENSOR FOR CURRENT SUPPLIED TO MEDICAL DEVICE LOADS

[75] Inventors: Richard K. Thompson, Englewood, Colo.; Ernesto Sevilla, Herkimer, N.Y.

[73] Assignee: Conmed Corporation, Utica, N.Y.

[*] Notice: The portion of the term of this patent subsequent to Jul. 11, 2012 has been disclaimed.

[21] Appl. No.: 69,359

[22] Filed: Jun. 1, 1993

Related U.S. Application Data

[63] Continuation-in-part of Ser. No. 9,598, Jan. 27, 1993, which is a continuation-in-part of Ser. No. 901,024, Jun. 19, 1992, Pat. No.

[51] Int. Cl.$^6$ .............................................. G01R 31/02
[52] U.S. Cl. .................................. 324/713; 128/908; 606/32
[58] Field of Search ............... 324/158 P, 522, 611, 324/713, 718, 720; 128/908, 639–641; 606/32, 34, 35

[56] References Cited

U.S. PATENT DOCUMENTS

| | | | |
|---|---|---|---|
| 3,946,738 | 3/1976 | Newton et al. | 606/34 |
| 4,094,320 | 6/1978 | Newton et al. | 606/35 |
| 4,437,464 | 3/1984 | Crow | 606/35 |
| 4,532,510 | 7/1985 | Bertrand et al. | 324/611 |
| 5,152,762 | 10/1992 | McElhenney | 606/35 |
| 5,246,439 | 9/1993 | Hebborn et al. | 606/35 |

*Primary Examiner*—Kenneth A. Wieder
*Assistant Examiner*—Christopher M. Tobin
*Attorney, Agent, or Firm*—Larson and Taylor

[57] ABSTRACT

A current sensing device enables sensing the current being delivered from a source to a load at a medical implement connected to the distal end of a primary conductor connected between the source and the load in situations wherein distributed capacitance between the primary conductor and a return path to the source prevents a measurement of current at the source end of the primary conductor from being an accurate measurement of the delivered current. The current sensing device includes a reference conductor which is located beside and is preferably twisted together with the primary conductor along the length thereof and which is connected to the medical implement load through a resistor at the load of a value such as to effectively electrically isolate the reference conductor from the load. A subtractor subtracts the current flowing through the reference conductor from the total load current flowing to the medical implement so as to offset the effect of the distributed capacitance and to thereby produce a current measurement corresponding to the delivered current. The subtractor can comprise a current transformer through which the conductors extend in opposing relation. An integrity detector monitors whether the reference conductor is intact.

7 Claims, 5 Drawing Sheets

LEAKAGE CAPACITANCE COMPENSATING CURRENT SENSOR FOR CURRENT SUPPLIED TO MEDICAL DEVICE LOADS

CROSS REFERENCES TO RELATED APPLICATION

This application is a continuation-in-part of application Ser. No. 08/009,598, filed on Jan. 27, 1993, and entitled "Current Sensor for Medical Devices Including Connector Cables" which, in turn, is a continuation-in-part of application Ser. No. 07/901,024 now U.S. Pat. No. 5,300,070, filed on Jun. 19, 1992, and entitled "Electrosurgical Trocar Assembly with Bi-Polar Electrode," which, in turn, is a continuation-in-part of application Ser. No. 07/853,149, now abandoned, filed Mar. 17, 1992, and entitled "Electrosurgical Trocar Assembly."

FIELD OF THE INVENTION

The present invention relates to medical systems and instruments wherein electrical current delivered to the load end of electrical cable or other electrical conductor, including but not limited to electrosurgical trocars and r.f. ablation devices, and, more particularly, to current sensor devices for determining the amount of current so delivered.

BACKGROUND OF THE INVENTION

There are a number of instances where it is necessary to determine the amount of current delivered to the distal end of an electrical conductor such as a cable. For example, the above-identified applications, the contents of which are hereby incorporated by reference, disclose an electrosurgical trocar assembly wherein a trocar includes an electrosurgical cutting element connected by a cable to an electrosurgical generator and wherein, in a preferred embodiment, it is desired to shut down the electrosurgical generator when the tip of the trocar penetrates through the wall of the body cavity involved (e.g., the peritoneum). As disclosed in these application, this can be done by sensing the current being delivered by the electrosurgical generator since this delivered current will change when penetration is achieved. Another example of where this is desirable is in connection with r.f. (radio frequency) ablation procedures where there is a need to tightly control delivery of electrosurgical current. The invention will be described below particularly with respect to electrosurgical trocar devices although it is to be understood that the invention is applicable to any situation where there is need to know the amount of a.c. current being delivered to a load at the end of an electrical conductor such as a cable.

Considering the problem to be solved in more detail, when the current being delivered is of high frequency and high voltage as is the current output produced by an electrosurgical generator, a measurement of the total current produced by the generator does not accurately indicate the actual current delivered to the distal end of the electrical connecting cable. The discrepancy or error is due to the distributed capacitance to the current return path of the generator. The current flows through the cable along the entire length thereof and the amount of current flow is determined by the voltage, frequency, distributed capacitance to ground (or return), and cable length. Thus, referring to FIG. 1 wherein an electrosurgical generator is indicated at G, a load impedance (e.g., the impedance of the tissue being operated on by an electrosurgical electrode or cutting element) is indicated at $Z_L$ and a shunt impedance representing the distributed capacitance to ground, i.e., the "leakage" capacitance, is indicated at $Z_{ca}$. The generator voltage is V and thus the total current, $I_t$, can be represented by the equation $I_t = V/Z_{ca} + V/Z_L$. Although the current delivered to the load can be derived by measuring V and $I_t$ and then subtracting out the effect of the capacitance, in many cases, and particularly in electrosurgery, the capacitance is unknown and actually varies with the position of the cable in an unpredictable manner, thereby making a simple current measurement at the generator end of the cable inaccurate.

SUMMARY OF THE INVENTION

In accordance with the invention, a current sensing device is provided which enables accurate measurement of the current actually being delivered from a source to a load at a medical instrument under circumstances such as those described above wherein a direct measurement of the current at the source side is inaccurate because the effect of distributed capacitance of the connecting cable or other connection between the source and load.

According to a preferred embodiment of the invention, a current sensing device is provided for sensing the A.C. current delivered from a source to a load formed at a medical implement connected to the distal end of a primary electrical conductor for supplying current to the medical implement load from the source wherein distributed capacitance between the primary conductor and a return path to the source prevents a measurement of current at the source end of the primary conductor from being an accurate measurement of the current delivered to the medical implement load, the current sensing device comprising a reference electrical conductor disposed beside the primary electrical conductor along the length thereof and connected to the medical implement load through an impedance at the load of a value such as to effectively electrically isolate the reference electrical conductor from the load and so that the current flowing through the reference electrical conductor is essentially due to distributed capacitance, and subtracting means for subtracting the current flowing through the reference conductor from the total load current flowing to the medical implement so as to offset the effect of the distributed capacitance and to thereby produce a current measurement corresponding to the current delivered to the medical implement load.

Preferably, the current sensing device further includes detector means for sensing whether the reference conductor is intact. In a preferred embodiment, the value of said impedance is a known value and the detector means comprises an impedance measuring device for sensing the current flow through the reference conductor. Advantageously, the impedance measuring device comprises a circuit connected across the primary conductor and the reference conductor and including a fixed voltage source, and a current measuring device connected in series with the fixed voltage source.

A plurality of capacitors are preferably connected in series with the primary and reference conductors so as to isolate induced d.c. current from the source delivering the a.c. current.

Preferably, the subtracting means comprises a magnetic subtraction arrangement. The magnetic subtraction arrangement advantageously comprises a current transformer, with the primary conductor extending through the current transformer in a first orientation and the reference conductor extending through the current transformer in an opposing orientation so that the output of the current transformer is related to the difference in the current flow through the primary and reference conductors.

Other features and advantages of the invention will be set forth in, or apparent from, the following detailed description of preferred embodiments of the invention.

DESCRIPTION OF THE PREFERRED EMBODIMENTS

Figure 2:
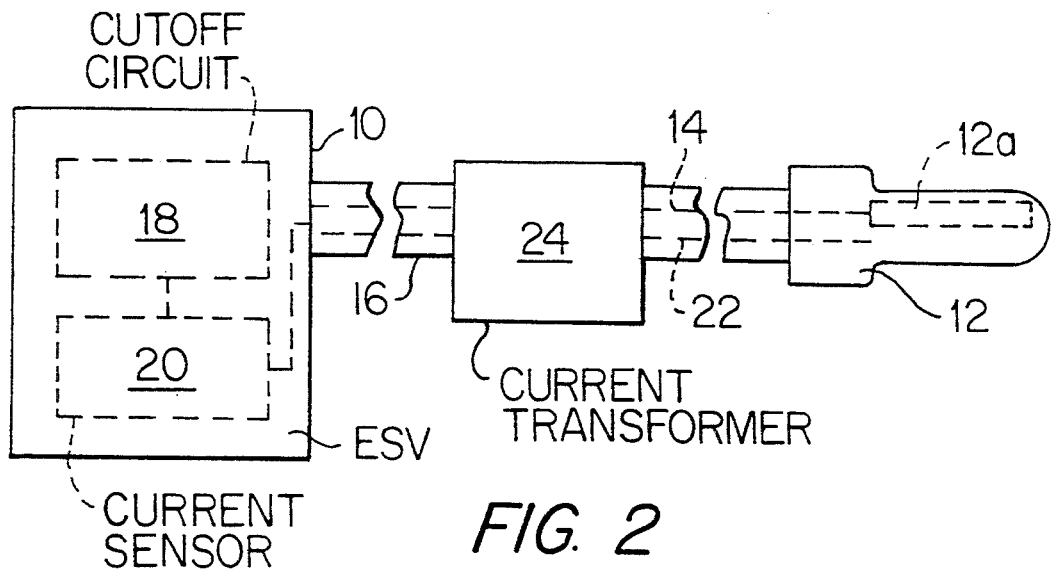
FIG. 2 is a highly schematic block diagram of a first embodiment of the invention.

Referring to FIG. 2, a block diagram is provided of one preferred embodiment of the current sensing device or system of the invention as incorporated in an electrosurgical trocar assembly. The trocar assembly includes an electrosurgical unit or generator (ESU) 10 connected to an electrosurgical trocar 12 such as that disclosed in the above-identified applications through a connecting wire or conductor 14 of a connector cable 16. The ESU 10 includes a shutdown or cutoff circuit 18 which can, for example, correspond to that described in the above-identified applications and which provides for shutdown of the ESU 10, i.e., suspension or cutoff of the power delivered to the trocar 12 from the ESU 10, upon penetration of the trocar tip through the wall of the cavity in question (e.g., the abdominal wall). In this embodiment, a current sensor unit 20 is located with the ESU 10 although a separate control unit or control box could be provided.

As discussed above, an important problem with systems wherein sensing of the current takes place at the ESU (or at a remote control box) is that, at the frequencies involved, the connecting cable 16 presents a sizeable and varying "leakage" impedance that makes detection of the shutoff point difficult. According to the embodiment of FIG. 2 and as is also schematically in FIG. 3 and in FIGS. 4 to 6, a reference wire or conductor 22 is also provided in cable 16 in parallel with, i.e., beside and closely coupled to, the wire 14 carrying the r.f. current to the trocar 12 but is not connected to the cutting element 12a of the trocar 12. As a result, the current sensor 20 can be made to sense the difference between the load conditions seen by the "hot" (primary) wire or conductor 14 and the reference wire or conductor 22.

Figure 1:
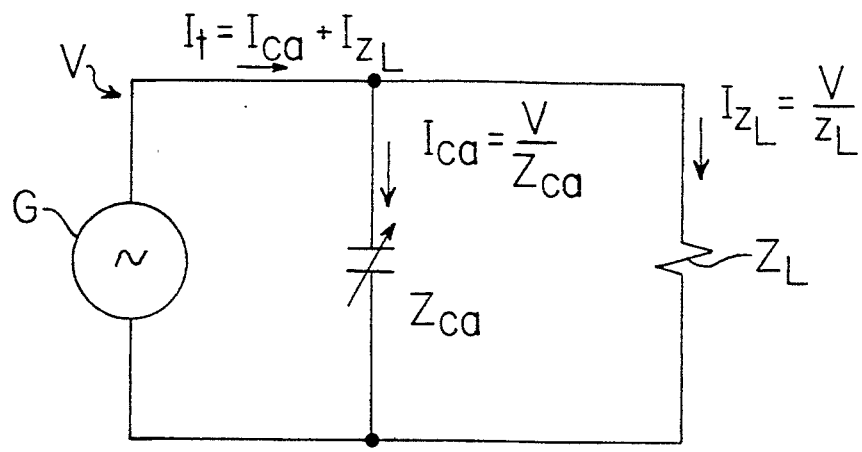
FIG. 1 is, as described above, a schematic circuit diagram illustrating the effect of distributed capacitance on a measurement of the current delivered to a load from a generator.
Figure 3:
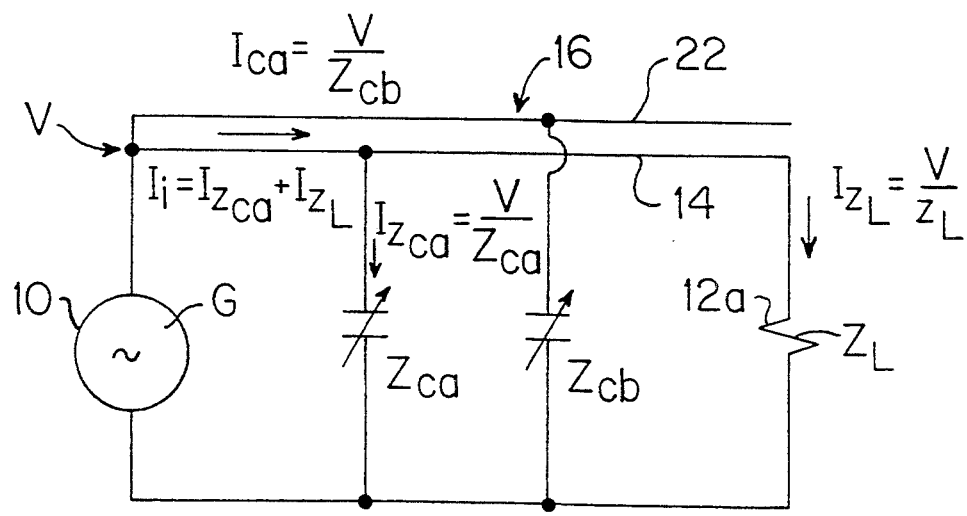
FIG. 3 is a schematic circuit diagram, similar to that of FIG. 1, of the first embodiment of the invention.

As noted above, this arrangement of the reference wire 22 is also shown schematically in FIG. 3, which is a schematic circuit diagram similar to that of FIG. 1 and in which similar notation is used. As illustrated, the second or reference electrical conductor 22 is placed next to the primary or "hot" conductor 14 in such a manner that the current coupled from the reference wire 22 to the current return of the generator 10, other than at the end of the reference wire 22, is equivalent to the current coupled from the primary conductor 14 to the current return of the generator 10. The preferred technique for achieving this is to connect both conductors 14 and 22 to the generator current source and to twist the conductors 14 and 22 together.

As explained above, only the primary electrical conductor 14 is actually connected to a load ($Z_L$) at the distal end, with the secondary conductor terminating just before the load. The secondary or reference conductor 22 will have an impedance to ground, $Z_{cb}$, due to leakage capacitance, i.e., distributed coupling capacitance. The closer the secondary conductor 22 is to the end of conductor 14 the better the current loss through capacitive coupling will match. Because both current losses are made equal, the total current delivered to the tip can be determined, as stated above, by subtracting the leakage current in the secondary wire 22 from the total current in the primary wire 14, i.e., $I_L = I_1 - I_{cb}$. Because $I_1$ and $I_{cb}$ can be accurately measured at the generator side of cable 16, if it is ensured that $I_{cb} = I_{ca}$, $I_L$ can be then ascertained by subtracting $I_{cb}$ from $I_1$.

Figure 4:
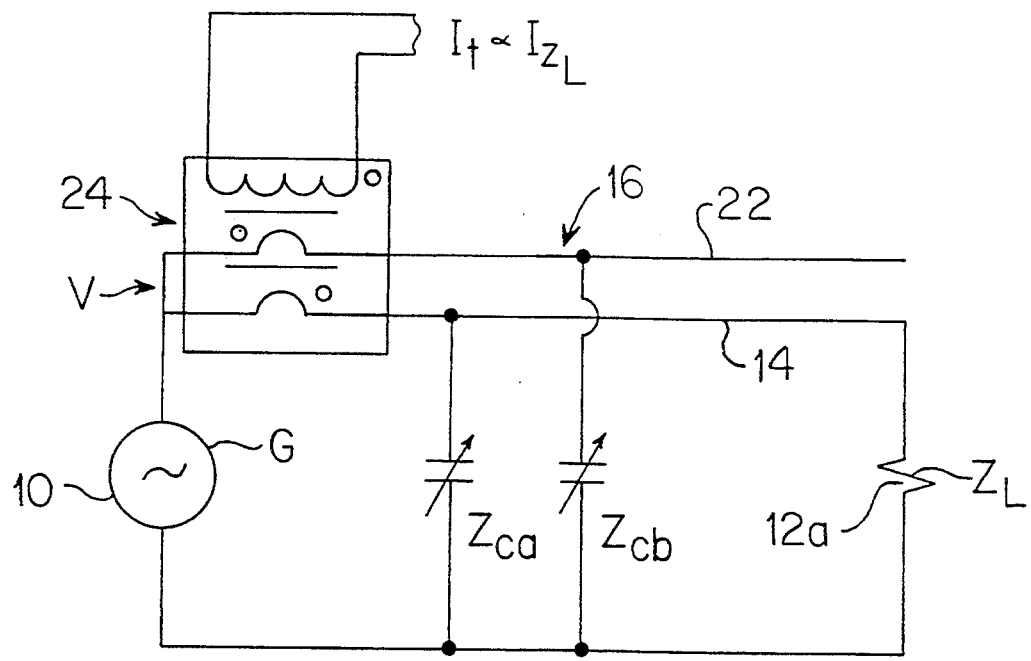
FIG. 4 is a schematic circuit diagram similar to that of FIG. 3, but including a magnetic subtraction arrangement.

Several methods can be used to provide the subtraction referred to above, and in the embodiment of FIG. 2, as is illustrated in the schematic circuit diagram of FIG. 4, this can be done by magnetic subtraction, using a current transformer 24. In particular, the primary conductor 14 is placed through the transformer 24 in a given orientation while the secondary or reference conductor 22 is placed through the same transformer 24 in an opposing orientation, as is illustrated in FIG. 4. The output of current transformer 24 will thus be the difference between the current in the primary conductor 14 and the secondary conductor 22, i.e., the current delivered to the load $Z_L$ (cutting element 12a). It is this current that will be sensed by current sensor 20 and used to control cutoff circuit 18.

It is noted that if the secondary conductor 16 is broken the current readings will be inaccurate. For this reason, the invention also concerns the provision of techniques to determine whether the secondary conductor 22 is intact. In particular, the controller that senses the current and controls the electrosurgical generator 10 (represented schematically by units 18 and 20 in FIG. 2) is set to produce an alarm signal and to turn off the electrosurgical generator 10 if a minimum level of current in the secondary or reference conductor 22 is not sensed when activation of the ESU 10 is commenced. In the magnetic subtraction embodiment of FIGS. 2 and 4, this is accomplished, as shown in FIG. 5, by adding a further current transformer 26 through which only the secondary conductor 22 passes.

Figure 5:
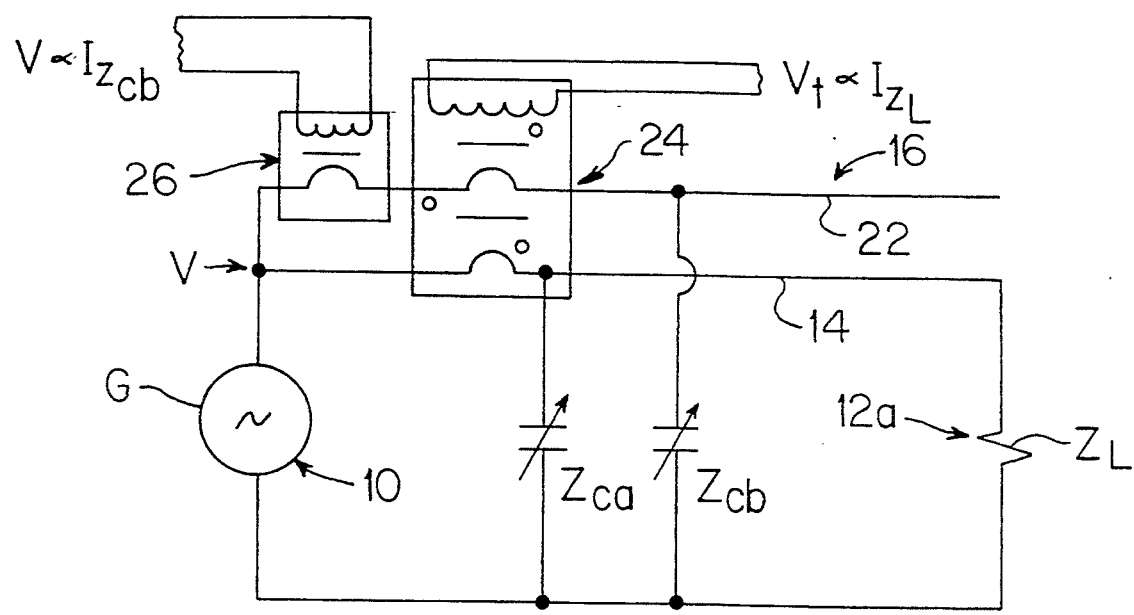
FIG. 5 is a schematic circuit diagram similar to FIG. 4, but including a reference conductor integrity detector.
Figure 6:
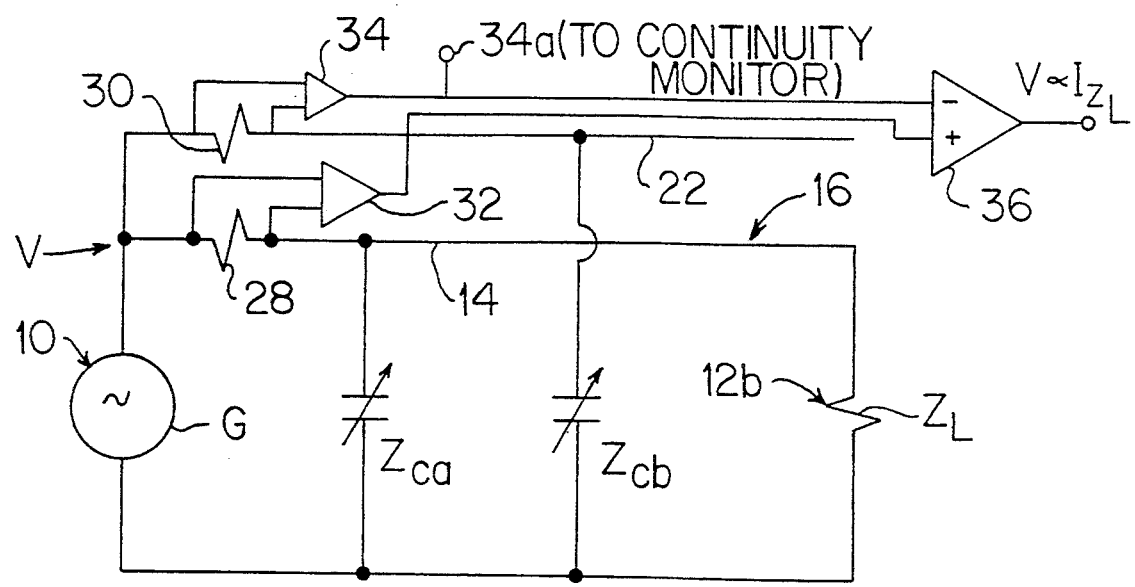
FIG. 6 is a schematic circuit diagram similar to that of FIG. 1 in accordance with a further implementation of the first embodiment of the invention.

A further method of providing the desired current subtraction is illustrated in FIG. 6 which is similar to FIGS. 4 and 5 but in which transformer 24 is replaced by impedances 28 and 30 connected in the respective conductors 4 and 22 Differential voltage amplifiers 32 and 34 are connected across the respective impedances 28 and 30 and the outputs of the two amplifiers are connected to a further differential amplifier 36. Thus, the output of the latter is a voltage $V_o$ proportional to the load current. Monitoring whether conductor 22 is intact can also be achieved with the embodiment of FIG. 6 by, for example, adding an output connection 34a at the output of differential voltage amplifier 34 so as to measure just the voltage across the impedance 30 placed in the secondary conductor 22.

Figure 7:
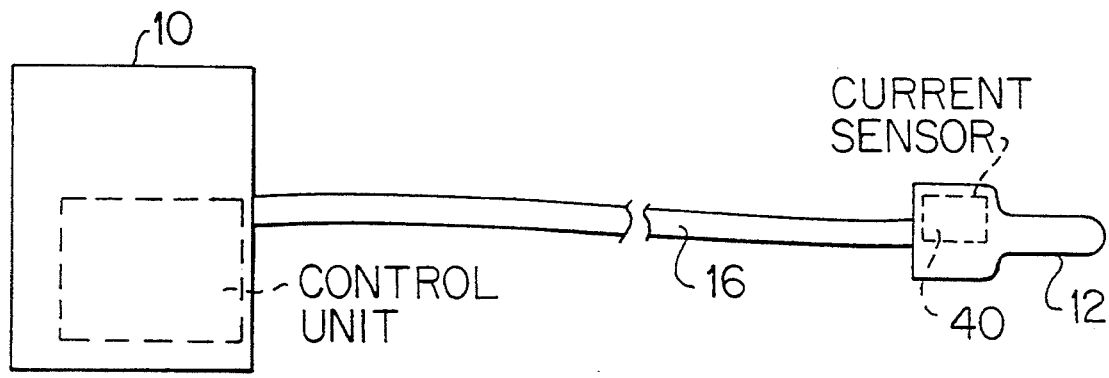
FIG. 7 is a highly schematic block diagram of yet another embodiment of the invention.

Referring to FIG. 7, a further approach to the basic problem discussed above is illustrated. In this embodiment, as is illustrated schematically in FIG. 7, a current sensor 40 is placed at the distal end of the primary or "hot" conductor 14 (there is no reference conductor). If the output of sensor 40 is not affected by capacitance to ground, i.e., where the output is a digital signal, light (through a fiber optic cable), a transmitted r.f. signal or a DC voltage corresponding to current, the load current can be accurately sensed. Any one of a number of different types of current sensors can be used, including a thermal sensor and thermistor (or thermocouple) for converting the signal into a useable voltage, a current transformer with rectification and filtering to convert the current to a DC voltage, and the like.

Figure 8:
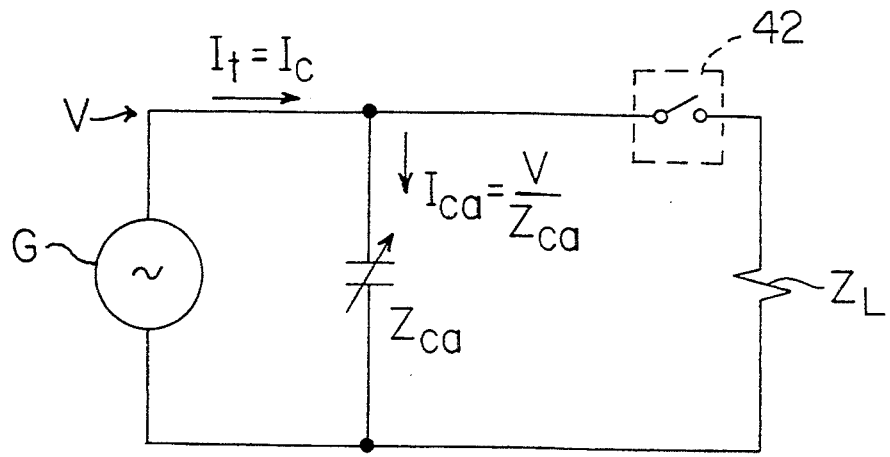
FIG. 8 is a schematic circuit diagram similar to FIG. 1 of a further embodiment of the invention.

Referring to FIG. 8, a further embodiment of the invention is shown. FIG. 8 is similar to FIG. 1 and, again, similar notation has been used. FIG. 8 differs from FIG. 1 in that in order to overcome the problem discussed above, a switching unit or switch 42 is provided at the load end of the cable, i.e., at the end containing load impedance $Z_L$. In operation, the switch 42 is left open thereby forcing the load current to a known zero and the generator G (corresponding to ESU 10 of FIG. 2) is caused to produce voltage. The resulting current can be measured and used as a reference level, assuming that the movement of the connecting cable (e.g., a cable corresponding to cable 16) is minimal, so that the distributed capacitance is constant. This reference current level is subtracted from the total current produced when the switch 42 is activated (closed) and thus current is delivered to the load (and to the distributed capacitance). The result of the open switch measurement can also be used to calculate the distributed capacitance and the resultant calculated value then used to determine the current delivered to the load.

Figure 9:
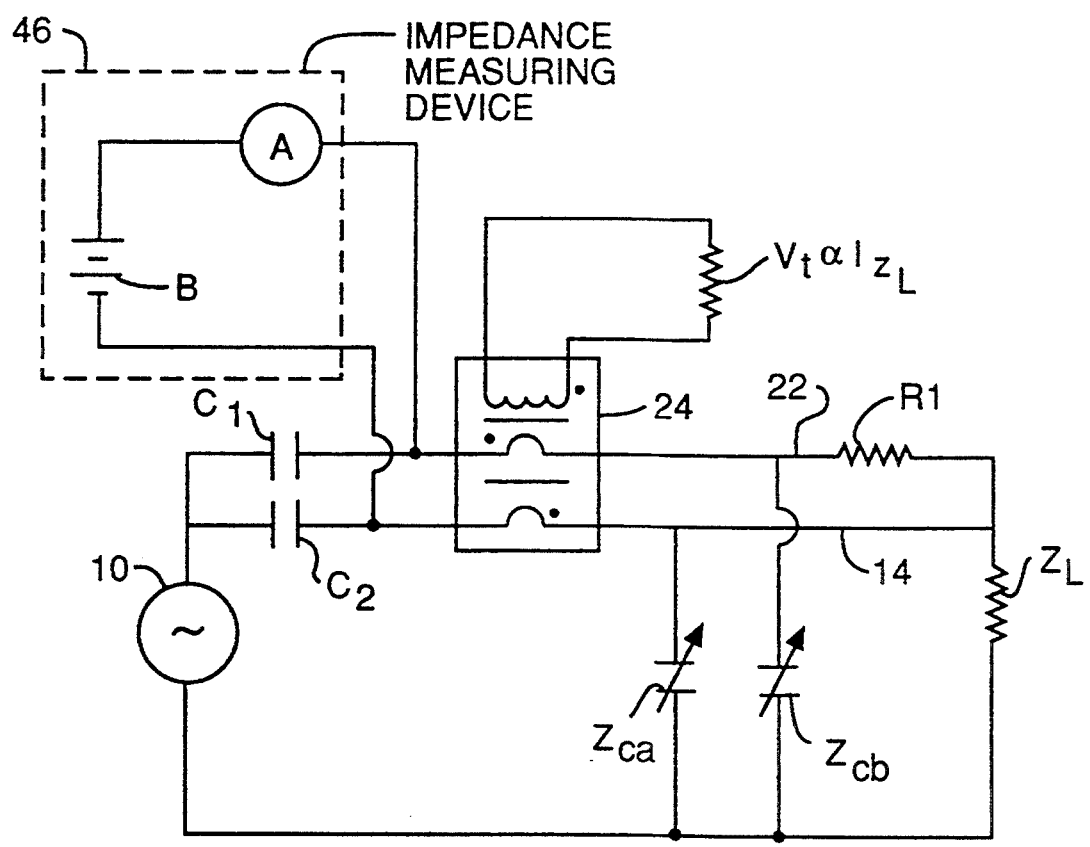
FIG. 9 is a schematic circuit diagram similar to that of FIGS. 4 and 5 of still another embodiment of the invention.

Referring to FIG. 9, a further important embodiment of the invention is shown. It will be appreciated from the foregoing discussion that while the two conductors 14 and 22 are shown as being unconnected at the load end, i.e., conductor 22 is shown as not being connected to the load, it would be possible to produce essentially the same effect by connecting a high value resistor or other impedance between the reference conductor 22 and the load. This is what is done in the embodiment of FIG. 9 wherein conductor 22 is connected to the load $Z_L$ through a resistor R1 of a known value which is of a high enough value to be transparent to the cancellation circuit but low enough to enable monitoring of the cancellation or reference conductor 22 to ensure that the conductor 22 is intact. In this embodiment, capacitors C1 and C2 are also added to the basic circuit illustrated in FIGS. 4 and 5 in order to isolate the induced d.c. current from the generator 10.

The continuity of monitoring circuitry of FIG. 9 is also different from that of FIG. 5. In the embodiment of FIG. 9, an impedance measuring unit or circuit 46 is provided in the form of a battery B which provides a fixed d.c. voltage and a current measuring device or ammeter A and is connected to the two conductors 14 and 22. Resistor R1 is added at the tip of the device and if impedance measuring unit 46 determines that R1 is connected in the circuit and is of the correct value (as determined by the reading of ammeter A), it can be assumed that both conductors 14 and 22 are intact.

It should be noted that with appropriate filtering and isolation, the impedance measuring device could also use a.c. current with good results. In accordance with a further variation on the illustrated embodiment of FIG. 9, a second, separate current could be provided through the current transformer 24 of a polarity opposite to the current generated by the impedance measuring device 46 so as to prevent d.c. saturation of current transformer 24.

Figure 10:
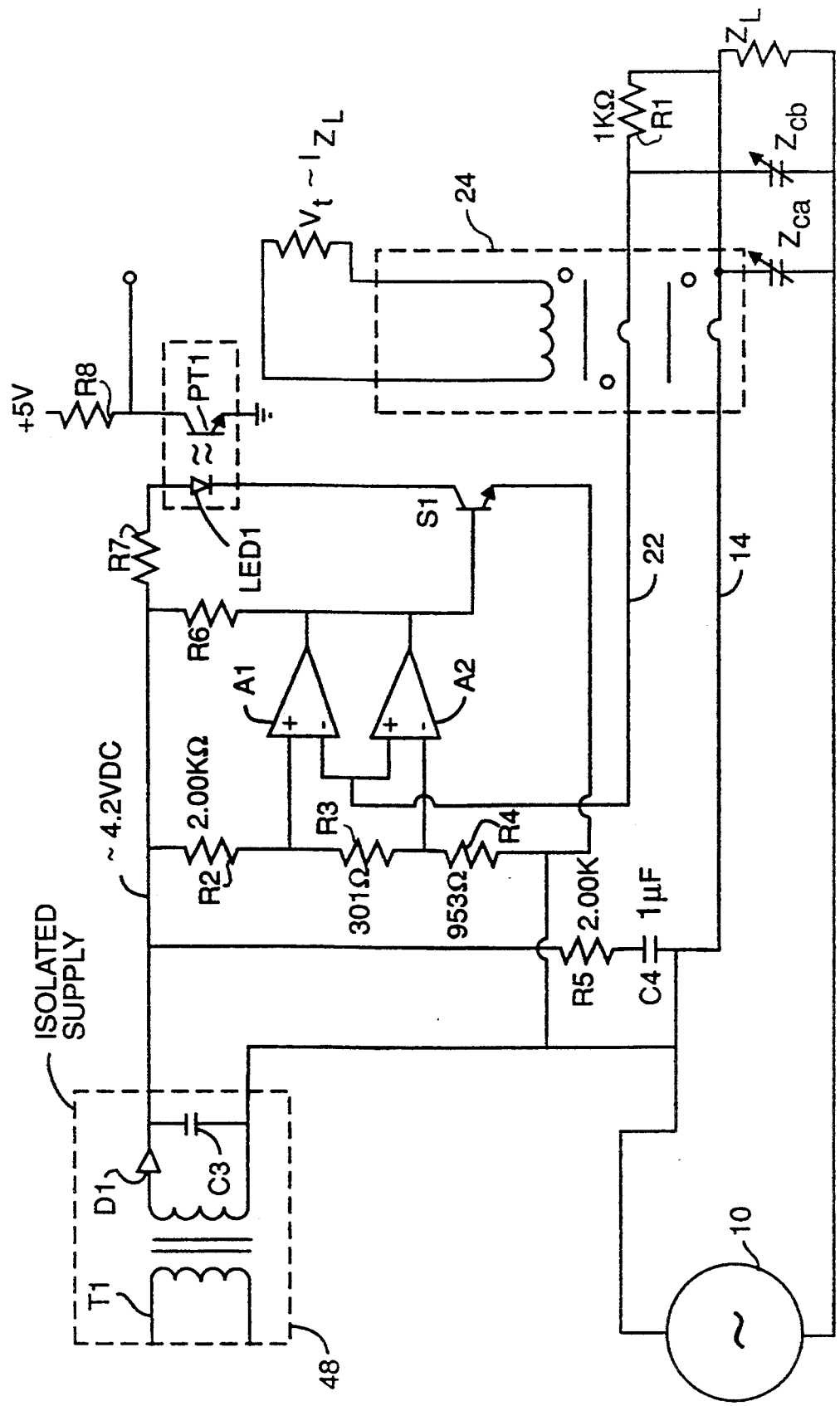
FIG. 10 is a is a specific implementation of the embodiment of FIG. 9.

Referring to FIG. 10, a specific implementation of the embodiment of FIG. 9 is shown. The circuitry of FIG. 10 includes an isolated power supply 48, including a transformer T1, a series diode D1 and a shunt capacitor C3, connected across three series connected resistors R2, R3 and R4. The inputs of a pair of operational amplifiers A1 and A2 connected as shown to junctions between the resistors R2, R3 and R4 and to conductor 22 through a branch connection. As illustrated, one side of the power supply 48 is connected to conductor 14 through a resistor R5 and a capacitor C4, and from a junction point between resistor R5 and capacitor C4 to conductor 22. The outputs of operational amplifiers A1 and A2 are connected between the one of supply 48 (through a resistor R6) and the base of a transistor S1 the emitter of which is connected to the other side of supply 48. The collector of transistor S1 is connected in series with a light source LED1 which is connected to the one side of supply 48 through a resistor R7. A light receiver in the form of a phototransistor PT1 receives light from source LED1. The emitter of phototransistor PT1 is connected to ground and the collector thereof is connected through a resistor R8 to a supply terminal (+5V). An output connection is provided between resistor R8 and the collector of phototransistor PT1.

The overall operation of the embodiment of FIG. 10 is similar to that of FIG. 9 and the operation of current transformer 24 is the same. Typical, non-limiting values used in an exemplary implementation are shown in FIG. 10. It is noted that a capacitor corresponding to capacitor C2 of FIG. 9 has been omitted and is not used in FIG. 2 since an ESU (corresponding to source 10) is already capacitively isolated at the output thereof.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A current sensing device for sensing the A.C. current delivered from a source to a load formed at a medical implement connected to the distal end of a primary electrical conductor for supplying current to the medical implement load from the source wherein distributed capacitance between the primary conductor and a return path to the source prevents a measurement of current at the source end of the primary conductor from being an accurate measurement of the current delivered to the medical implement load, said current sensing device comprising a reference electrical conductor disposed beside the primary electrical conductor along the length thereof and connected to the medical implement load through an impedance at the load of a value such as to effectively electrically isolate the reference electrical conductor from the load and so that the current flowing through the reference electrical conductor is essentially due to the distributed capacitance, and subtracting means for subtracting the current flowing through said reference conductor from the current flowing in the primary conductor at the source end so as to offset the effect of the distributed capacitance and to thereby produce a current measurement corresponding to the current delivered to the medical implement load.

2. A current sensing device as claimed in claim 1 further comprising detector means for sensing whether said reference conductor is intact.

3. A current sensing device as claimed in claim 2, wherein the value of said impedance is a known value and said detector means comprises an impedance indicating device for sensing the current flow through said reference conductor.

4. A current sensing device as claimed in claim 3 wherein said impedance indicating device comprises a circuit connected across the primary conductor and the reference conductor and including a fixed voltage source and a current measuring device connected in series with said fixed voltage source.

5. A current sensing device as claimed in claim 4 further comprising capacitors connected in series with said primary and reference conductors so as to isolate induced d.c. current from the source delivering the a.c. current.

6. A current sensing device as claimed in claim 1 wherein said subtracting means comprises a magnetic subtraction arrangement.

7. A current sensing device as claimed in claim 6 wherein said magnetic subtraction arrangement comprises a current transformer, said primary conductor extending through said current transformer in a first orientation and said reference conductor extending through said current transformer in an opposing orientation so that the output of the current transformer is related to the difference in the current flow through the primary and reference conductors.

* * * * *